(12) United States Patent
Boodaghians et al.

(10) Patent No.: US 9,550,006 B2
(45) Date of Patent: Jan. 24, 2017

(54) SYSTEMS AND METHODS FOR TREATMENT OF CABIN SURFACES AND AIR

(71) Applicant: MAG Aerospace Industries, LLC, Carson, CA (US)

(72) Inventors: Razmik B. Boodaghians, Glendale, CA (US); Shane Nazari, Glendale, CA (US); Christina Ortolan, Long Beach, CA (US)

(73) Assignee: MAG Aerospace Industries, LLC, Carson, CA (US)

( * ) Notice: Subject to any disclaimer, the term of this patent is extended or adjusted under 35 U.S.C. 154(b) by 0 days.

(21) Appl. No.: 14/865,685

(22) Filed: Sep. 25, 2015

(65) Prior Publication Data

US 2016/0089459 A1    Mar. 31, 2016

Related U.S. Application Data

(60) Provisional application No. 62/055,802, filed on Sep. 26, 2014.

(51) Int. Cl.
| | |
|---|---|
| *A61L 2/10* | (2006.01) |
| *A61L 9/20* | (2006.01) |
| *B64D 11/00* | (2006.01) |
| *A61L 2/24* | (2006.01) |

(52) U.S. Cl.
CPC .. *A61L 2/10* (2013.01); *A61L 9/20* (2013.01); *B64D 11/00* (2013.01); *A61L 2/24* (2013.01); *A61L 2202/25* (2013.01)

(58) Field of Classification Search
CPC ........... A61L 2/10; A61L 2/24; A61L 2202/25
See application file for complete search history.

(56) References Cited

U.S. PATENT DOCUMENTS

| | | | | |
|---|---|---|---|---|
| 6,470,512 | B1 * | 10/2002 | Lau | A47K 3/30 4/612 |
| 8,226,887 | B2 * | 7/2012 | Harmon | A61L 2/10 250/455.11 |
| 2004/0021425 | A1 * | 2/2004 | Foust | G09F 9/33 315/169.3 |
| 2007/0053188 | A1 * | 3/2007 | New | A61L 9/20 362/276 |
| 2008/0127411 | A1 * | 6/2008 | Hoffjann | B60R 15/02 4/664 |

(Continued)

FOREIGN PATENT DOCUMENTS

| | | |
|---|---|---|
| DE | 102012006972 A1 | 10/2013 |
| EP | 2492195 A1 | 8/2012 |
| EP | 2772272 A1 | 9/2014 |

OTHER PUBLICATIONS

International Search Report and Written Opinion in International Application No. PCT/US2015/052208 dated Nov. 17, 2015, 9 pages.

*Primary Examiner* — Wyatt Stoffa
(74) *Attorney, Agent, or Firm* — Kilpatrick Townsend & Stockton LLP; Dean W. Russell; Kristin M. Crall

(57) ABSTRACT

Embodiments relate generally to systems and methods for treating passenger transportation vehicle cabin surfaces and surrounding air. The methods may use organic LEDs to produce ultraviolet light. Systems may be provided to ensure safety and operation of the air treatment only when passengers and personnel are not present in the cabin.

8 Claims, 2 Drawing Sheets

(56) References Cited

U.S. PATENT DOCUMENTS

| | | | |
|---|---|---|---|
| 2008/0286145 A1* | 11/2008 | Ratcliffe | A61L 2/10 422/24 |
| 2009/0191100 A1* | 7/2009 | Deal | A61L 2/10 422/105 |
| 2012/0187313 A1* | 7/2012 | Clark | A61L 2/10 250/492.1 |
| 2012/0221192 A1* | 8/2012 | Seibt | B64D 11/02 701/29.1 |
| 2012/0230867 A1* | 9/2012 | Kerr | A61L 2/10 422/24 |
| 2013/0175460 A1* | 7/2013 | Farren | A61L 2/10 250/504 R |
| 2013/0234041 A1* | 9/2013 | Deal | A61L 2/10 250/455.11 |
| 2014/0017135 A1 | 1/2014 | Boodaghians et al. | |
| 2014/0034912 A1* | 2/2014 | Liu | H01L 51/5036 257/40 |
| 2014/0059796 A1* | 3/2014 | Boodaghians | A61L 2/10 15/339 |
| 2014/0241941 A1* | 8/2014 | Kreitenberg | B64D 11/0007 422/24 |
| 2014/0271352 A1* | 9/2014 | Stewart | A61L 2/10 422/24 |

\* cited by examiner

SYSTEMS AND METHODS FOR TREATMENT OF CABIN SURFACES AND AIR

CROSS REFERENCE TO RELATED APPLICATIONS

This application claims the benefit of U.S. Provisional Application Ser. No. 62/055,802, filed Sep. 26, 2014, titled "System and Methods for Treatment of Cabin Surfaces and Air," the entire contents of which are hereby incorporated by reference.

FIELD OF THE DISCLOSURE

Embodiments of the present disclosure relate generally to systems and methods for treating passenger transportation vehicle cabin surfaces and surrounding air. The methods may use organic LEDs to produce ultraviolet light. Systems may be provided to ensure safety and operation of the air treatment only when passengers and personnel are not present in the cabin.

BACKGROUND

Aircraft and other passenger transportation vehicle facilities can transport infections, viruses, and bacteria across large distances. This transport can happen very rapidly, due to the very nature of travel. Passengers often travel when knowingly sick, and their coughing, breathing, and/or touching surfaces can spread germs to other passengers. Passengers also travel when, often unknowingly, they have been exposed to a virus or other airborne illness that can be spread rapidly.

Aircraft and other passenger transportation vehicles may often be cleaned between routes. This cleaning may simply be trash removal and straightening of the visual area. It is not often the case that the cleaning involves a thorough disinfection of the passenger cabin. Accordingly, many passenger transportation vehicle cabins have air and surfaces that may be contaminated with bacteria, viruses, mold, and/or other airborne illnesses. It is generally desirable for any cleaning systems to be safe and effective. Improved systems and methods for cleaning cabin surfaces and air are described herein.

BRIEF SUMMARY

Embodiments of the invention described herein thus provide systems and methods for treating and disinfecting passenger transportation vehicle cabin surfaces and surrounding air. The methods may use UV lights or organic LEDs (OLEDs) to produce ultraviolet light. The light may kill or otherwise disrupt bacteria, viruses, or airborne-based illnesses. Systems may be provided to ensure safety and operation of the air treatment only when passengers and personnel are not present in the cabin.

One proposed solution provided by the current assignee is described in U.S. Publication No. 2014/0017135 titled "Systems and methods for disinfecting air on board a passenger transport vehicle," the contents of which are incorporated herein by reference.

In one example, there is provided a cabin disinfection system, comprising: one or more UV OLED disinfection lights positioned in the cabin; and a safety system for activating the one or more UV OLED disinfection lights only when the cabin is empty of passengers and personnel. The one or more disinfection lights may be flexible organic LEDs. The one or more disinfection lights are installed along a floor surface of the cabin, along an upper channel of the cabin, by overhead bins, in an overhead lighting area above cabin seats, or in any other appropriate location. The one or more disinfection lights may be installed on a temporary structure, such as a roll-out mat or cart or other appropriate structure. The safety system may be a rotating or sliding panel, an external panel that may only activate the cabin disinfection system when a cabin door is closed, or any other appropriate system. The safety system may automatically turn the disinfection system off if the cabin door is opened. The safety system may be a time-delay auto shutoff function. In one example, the cabin disinfection system is installed on-board a passenger aircraft.

In another example, there is provided a method for disinfecting a cabin, comprising: providing one or more UV OLED disinfection lights positioned in the cabin; activating the one or more UV OLED lights only when the cabin is empty of passengers and personnel. The system further may further comprise a service panel external to the aircraft that is activated externally, a computer-based system, or any other appropriate activation system.

DETAILED DESCRIPTION

Embodiments of the present invention provide systems and methods for treating passenger transportation vehicle cabin surfaces and surrounding air. Specific embodiments may find particular use on-board an aircraft, and specifically in an aircraft cabin. Although cabin treatment for aircraft surfaces and air is described throughout the remainder of this document, it should be understood that the systems and methods described herein may be used on any passenger transportation vehicle or in any other environment that houses a large number of people and is desirably rapidly cleaned. It should also be understood that the systems described may be found to clean only surfaces, only air, or a combination thereof. The surfaces that may be optionally disinfected include but are not limited to hard surfaces, grooved surfaces, plastic, fabric, carpet, or any other type of surface present in a passenger cabin.

Figure 1:
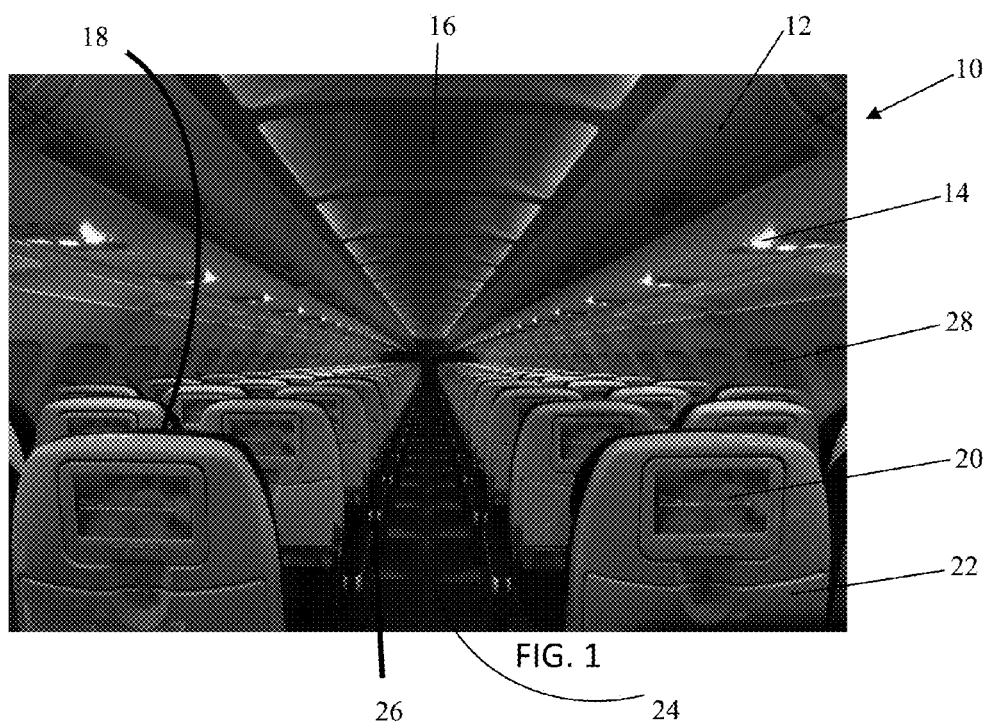
FIG. 1 shows a perspective view of a cabin interior with various locations where disinfection lights may be located.

As shown in FIG. 1, one embodiment described herein may be used on an aircraft passenger cabin 10. The cabin 10 will generally have overhead compartments 12, overhead lighting 14, ceiling panels 16, seats 18, in-flight entertainment (IFE) units 20, seat back trays 22, a floor surface 24, floor lighting 26, and windows with window covers 28. Cabins may also be provided with user interfaces at the seat level or remote controls for operating the IFE units. Cabins may also be provided with curtains dividing the economy cabin from the first class and/or business class cabin. Cabins may also be provided with monuments or storage areas for storing larger passenger items, such as foldable wheelchairs, or for hanging items, such as passenger jackets. Cabins may also be provided with one or more galleys for food and drink preparation and storage. Cabins may also be provided with one or more lavatories housing a toilet, a countertop, and a sink basin. Any or all of these cabin surfaces or areas are candidates for the disinfection systems and methods described herein.

Figure 2:
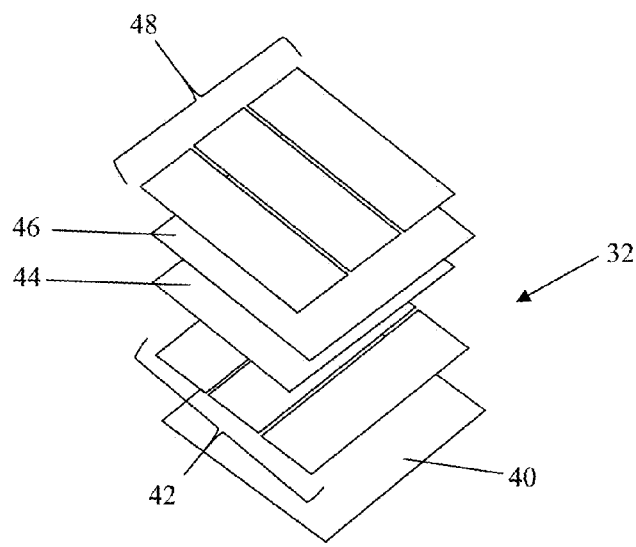
FIG. 2 shows a schematic perspective view of one embodiment of an organic LED that may be used in accordance with embodiments described herein.
Figure 3:
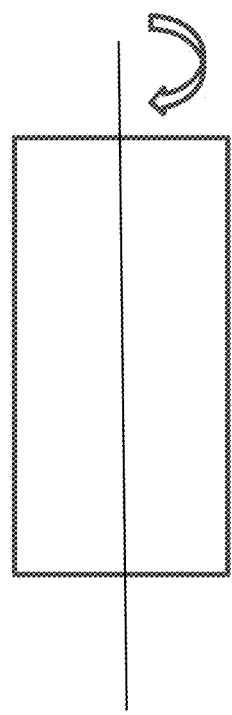
FIG. 3 shows a schematic view of one embodiment of a panel that rotates.

In one embodiment, the systems described may use ultraviolet (UV) light for disinfection. In a specific embodiment, the UV light used may be an organic LED (OLED). A specific example may include an OLED light that produces UV-C light. One exemplary OLED is illustrated by FIG. 2. Exemplary OLEDs may be manufactured and produced by a number of companies, and they may have any number of properties. The general goal is that the UV light or the OLED selected may operate within a wavelength that will disinfect the desired surfaces and/or the surrounding air. Exemplary wavelengths include but are not limited to approximately 240 to 285 nm. A single wavelength may be used throughout the disinfecting treatment process. In another example, it is possible to use varying wavelengths throughout the disinfecting treatment process in order to target various types of microorganisms, such as viruses, bacteria, and protozoans.

In use, the disinfection lights may be activated when the cabin 10 is empty of passengers or personnel. The lights may function to disinfect the cabin surfaces and cabin air. The lights are generally activated and allowed to treat the cabin surfaces and cabin air for a specified period of time. The disinfection sequence may take anywhere from about a few seconds to a few minutes, based on the system design.

The lights may generally be operated via a safety system. If a human eye is exposed to UV light, damage may occur, so the safety system may be configured to only allow the disinfection sequence to take place only when certain requirements are met. For example, it may be possible for the lights to be activated only when the passenger door is closed and/or only from an external service panel. This may prevent inadvertent activation when someone is on-board the aircraft. The service panel may have an optional indicator that indicates whether or not the disinfection lights are currently activated. In another example, it may be possible for the lights to be activated only by an external key to start the lights. In another example, it may be possible for the lights to be activated only when all aircraft systems are powered down. In another example, it may be possible for the lights to be activated only when the aircraft is parked. In another example, it may be possible for the lights to be activated only after a certain amount of time has elapsed since aircraft shut down and/or aircraft passenger door closing. In another example, it may be possible for the lights to be activated by a particular pre-programmed sequence. One exemplary sequence could be that once the aircraft is parked and the aircraft engines are off, certain checks may be made, and then the system may be activated only once the passenger door is closed and locked, using the auxiliary power unit to run the sequence. Combinations of the above safety features are also possible and considered within the scope of this disclosure.

In another example, the lights may have an automatic shut-off feature. The automatic shut-off feature may be time-based, such that after a certain number of minutes, the lights are automatically powered down. There may be provided a time delay before the lights may be turned back on again. In another example, if the lights are currently turned on, they may be automatically shut off upon unlocking and/or opening of the passenger door. In one example, it is possible for the automatic shut-off feature to have a built in redundancy. There may be provided circuits such that if the lights do not shut off during closure of a first circuit, they will shut off during closure of a second circuit.

One benefit if the UV light selected is an OLED is that OLEDs may be provided in any desired shape. For example, they may be installed on a flat or a curved surface. OLEDs may be flexible such that they can be manipulated to fit or conform to a curved surface. The OLEDs can be made in long continuous shapes where power connections may only be needed at one end. FIG. 2 illustrates one embodiment of a potential OLED light 32 that may be used in accordance with various embodiments described. It shows a substrate 40, an anode 42, a conductive layer 44 (which may be organic molecules or polymers), an emissive layer 46 ((which may be organic molecules or polymers), and a cathode 48. Although not shown, there may also be provided an optional cover for the light 32.

In one embodiment, one or more OLED disinfection lights may be installed along or with respect to one or more surfaces of the cabin 10. Exemplary locations are described in more detail below. In another embodiment, one or more UV OLED disinfection lights, may be installed on a temporary structure that may be moved into the cabin 10 by maintenance crew and then removed after the disinfection process has taken place. For example, it may be possible to provide roll-out OLED mats and/or carts. Such temporary structures may use aircraft power. Such temporary structures may be configured to be activated from outside the aircraft, such as via a service panel. Such temporary structures may be configured to be activated remotely.

If installed in the cabin 10, the one or more UV OLED disinfection lights 32 may be installed in or along existing light fixtures or tracks. For example, in one embodiment, one or more UV OLED disinfection lights 32 may be installed along the floor surface 24. In a specific example, the one or more UV lights 32 may be installed along the floor lighting track 26 on the aisles. It is possible for the floor lighting track 26 to contain typical emergency lighting, as well as the one or more UV OLED lights 32. For example, an emergency light may be alternated with a UV OLED light. They may be operated by the same system, but with different inputs indicating which set of lights should be activated, depending upon the situation. If the emergency lighting should be activated, only the emergency lights may be lit. If the disinfecting sequence is activated, only the UV OLED lights may be lit (although it should be understood that the emergency lighting may also be lit as well during a disinfecting process sequence).

In another embodiment, the one or more UV OLED disinfection lights 32 may be installed along the window or wall area. They may be installed as individual lights or along a channel containing a plurality of lights.

In another example, it is possible for one or more UV OLED disinfection lights 32 to be installed along upper channels. For example, the upper channels may be positioned along a location where the overhead compartments are located. For example, channels may be located at one or more joints where the overhead compartments meet the ceiling portion of the fuselage. Channels may be located in the lighting channels by the overhead bins. Channels may be located at the overhead user interface. Additionally or alternatively, it is also possible for the UV OLED disinfection lights 32 to be installed as individual lights.

In another embodiment, the one or more UV OLED disinfection lights 32 may be located on or near the location where the overhead compartment lights (and usually an attendant call button) are located, generally above cabin seats. The installation may be retrofit or the light may be positioned with the unit to be initially installed. However, there is generally not a user-activated option for activating the UV OLED light for safety reasons. It is possible to provide a single light per row of seats, it is possible to provide a single light per seat, or any combination thereof.

In another embodiment, the one or more UV OLED disinfection lights 32 may be positioned along or within regular ducting of the aircraft.

In another embodiment, the UV OLED disinfection lights 32 may be positioned on one or more rotating wall, ceiling, or floor panels, or otherwise provided as having a double-sided installation. In this example, the lights may be provided on panel(s) that are caused to rotate to expose the UV OLED disinfection lights when activated. For example, there may be provided OLEDs on one side of a wall panel and a typical cabin surface on the other side of the panel. For example, a floor or ceiling panel may have standard materials on one side for in-flight use, and the reverse side would have OLEDs. During normal flight or other non-disinfection times, the cabin surface panel will face the interior of the cabin. When disinfection is to be conducted, the panel may be activated to rotate to expose the OLEDs to the cabin, such that the OLED side is facing the interior of the cabin. Disinfection may take place under one or more of the safety precaution activation features described. Upon completion of disinfection, the one or more panels may be caused to rotate back to the cabin surface side. This can eliminate the need for a protective layer on the OLED because it will not face passenger or personnel or otherwise be subject to potential tampering or touching.

In another example, the UV OLED disinfection lights 32 may be positioned behind a sliding cover or panel. This can be to prevent the lights from being accessible or viewable when disinfection is not in process. When disinfection is to be conducted, the sliding cover or panel can be retracted to expose the lights for disinfection. When disinfection is complete, the sliding cover or panel can be moved to cover the lights.

In any of the examples described, it is possible for the OLED to be a flexible light, such that it can be bent to accommodate and/or fit with respect to a curved or non-standard surface. The OLEDs may be provided in strips, sheets, or as single point light sources. There may be a protective layer provided over the light.

The UV OLED disinfection light system may rely on the same power as traditional cabin lighting. In other examples, the light system may rely on alternate sources of power, such as an auxiliary power unit or other options.

Changes and modifications, additions and deletions may be made to the structures and methods recited above and shown in the drawings without departing from the scope or spirit of the disclosure or the following claims.

What is claimed is:

1. A cabin disinfection system, comprising:
   one or more UV OLED disinfection lights positioned in the cabin, the one or more UV OLED disinfection lights positioned on a panel that rotates, such that a first side of the panel comprises the one or more UV OLED disinfection lights and a second side of the panel comprises a cabin surface material; and
   a safety system for activating the one or more UV OLED disinfection lights only when the cabin is empty of passengers and personnel,
   wherein during disinfection, the first side of the panel is caused to face the cabin, and when disinfection is complete, the panel is rotated so that the second side of the rotating structure faces the cabin.

2. The system of claim 1, wherein the one or more disinfection lights comprise flexible organic LEDs.

3. The system of claim 1, wherein the safety system comprises an external service panel that may only activate the cabin disinfection system when a cabin door is closed.

4. The system of claim 3, wherein the safety system automatically turns the disinfection system off if the cabin door is opened.

5. The system of claim 1, wherein the safety system comprises a time-delay auto shutoff function.

6. The system of claim 1, installed on-board a passenger aircraft.

7. A method for disinfecting a cabin of an aircraft, comprising:
   activating a system comprising
      one or more UV OLED disinfection lights positioned in the cabin, the one or more UV OLED disinfection lights positioned on a panel that rotates, such that a first side of the panel comprises the one or more UV OLED disinfection lights and a second side of the panel comprises a cabin surface material, wherein the first side of the panel is configured to be rotated to face the cabin for disinfection; and
      a safety system for activating the one or more UV OLED disinfection lights only when the cabin is empty of passengers and personnel;
   wherein activating the system occurs only when an aircraft cabin door is shut and the aircraft cabin is empty of passengers and personnel.

8. The method of claim 7, wherein during activation for disinfection, the first side of the panel is caused to face the cabin, and when disinfection is complete, the panel is rotated so that the second side of the panel faces the cabin.

* * * * *